United States Patent
Baker et al.

[11] Patent Number: 5,139,328
[45] Date of Patent: Aug. 18, 1992

[54] NONCONTACT HEMATOCRIT READER APPARATUS AND METHOD

[75] Inventors: Charles D. Baker, Sandy; Owen D. Brimhall, South Jordan; Thomas J. McLaughlin, Salt Lake City, all of Utah

[73] Assignee: Separation Technology, Inc., Altamonte Springs, Fla.

[21] Appl. No.: 670,691

[22] Filed: Mar. 18, 1991

Related U.S. Application Data

[63] Continuation of Ser. No. 356,191, May 24, 1989, abandoned.

[51] Int. Cl.⁵ .................. G01N 33/48; G01N 31/02
[52] U.S. Cl. .......................... 356/39; 73/570; 73/61.63; 73/61.49; 356/40
[58] Field of Search .............. 356/36, 73, 39–42, 356/244, 246, 318, 441, 442, 443, 440, 432, 433; 73/61.1 R, 61.4, 53, 570

[56] References Cited

U.S. PATENT DOCUMENTS

| | | | |
|---|---|---|---|
| 3,561,877 | 2/1971 | Nakada et al. | 356/39 |
| 4,609,991 | 9/1986 | Minton et al. | 350/318 |
| 4,848,900 | 7/1989 | Kuo et al. | 73/61.4 |
| 4,854,170 | 8/1989 | Brimhall et al. | 73/570 |
| 4,887,458 | 12/1989 | Baker et al. | 73/61.4 |

*Primary Examiner*—Richard A. Rosenberger
*Assistant Examiner*—Hoa Pham
*Attorney, Agent, or Firm*—J. Winslow Young

[57] ABSTRACT

An automatic hematocrit reader wherein a sample of blood in a microhematocrit capillary tube is banded with a standing wave from an ultrasonic transducer. A light source and photocell combination is used to determine the relative thicknesses of the bands of red blood cells and the bands of plasma. The hematocrit of the sample of blood is electronically calculated from this data. A calibration strip is included so that the device is calibrated each time the hematocrit is determined. The device includes a mechanical interlock/eject system for the microhematocrit capillary tube and is specifically configured so that the operator does not handle or even touch the microhematocrit capillary tube.

11 Claims, 3 Drawing Sheets

NONCONTACT HEMATOCRIT READER APPARATUS AND METHOD

This application is a continuation application of our copending application Ser. No. 07/356,191 filed May 24, 1989 for Non Contact Hematocrit Reader Apparatus and Method, now abandoned.

1. Field of the Invention

This invention relates to an apparatus and method for determining the hematocrit of a sample of blood and, more particularly, to a noncontact hematocrit reader apparatus and method that provides a fast, accurate hematocrit reading without undue exposure of the operator to the blood.

2. The Prior Art

Hematocrit is a measure of the volume fraction that red blood cells occupy in the blood. Conventionally, a drop of blood is drawn by capillary action into a microhematocrit capillary tube, the end of which is then plugged with a clay-like material. Under centrifugation the incrementally greater density of the red blood cells results in their being packed into the lower end of the tube with the plasma being displaced toward the upper end of the tube. The hematocrit is calculated by determining the ratio of the length of the red blood cell volume to the total length of the blood sample times one hundred.

Blood loss (whether through trauma, gastrointestinal bleeding, or during surgery) can be discovered promptly if the attending medical personnel have immediate access to accurate hematocrit readings at regular intervals. Current methods of measuring hematocrit require at least five to ten minutes and involve access to the necessary centrifuge apparatus. Accordingly, emergency medical personnel such as civilian paramedics and military medics are not able to obtain hematocrit information in the field while treating trauma cases because a) the current method using centrifugation is time consuming and fairly labor intensive, and b) the required high speed centrifuge apparatus is a poor candidate for field use since it is expensive, bulky, heavy, and yet, fragile.

Additionally, the use of hematocrit information for the treatment of a trauma or gastrointestinal bleeding in a hospital is not satisfactory since even an emergency or "stat hematocrit" requires at least five minutes centrifugation in conjunction with significant technician time and labor. Due to the cost of the centrifugation apparatus it is usually placed in centralized locations for access by various users. The end result is that an additional time increment (beyond the centrifugation time) is required to transfer the microhematocrit capillary tube containing the sample to the laboratory where the centrifuge is located, obtain the hematocrit reading and then transmit the resulting hematocrit reading back to the appropriate medical personnel. This time factor is further compromised severely by the fact that in an endeavor to save technician labor several samples will be collected over a period of time so that all these samples can be processed in the centrifugation apparatus at the same time.

The increase in the prevalence of the virus responsible for the condition referred to as Acquired Immune Deficiency Syndrome (AIDS) has resulted in extensive changes in the manner by which blood products are handled. In particular, extreme care is taken to guard against inadvertent contact with blood, for example, through accidental puncture, or the like. However, until the introduction of the present invention there has been no significant change in the technique by which a hematocrit is obtained particularly with regard to handling of a blood-filled microhematocrit capillary tube. For example, the microhematocrit capillary tube is held in the hand while the blood is drawn into the tube by capillary action. The operator then punches the end of the tube into the clay-like plugging material prior to directing the tube for further processing. At any time during this handling of the blood-filled, microhematocrit capillary tube there is an inherent risk that the tube will break allowing a broken piece to puncture the skin of the operator after tearing the protective glove.

In view of the foregoing it would be a significant advancement in the art to provide a fast, convenient apparatus and method for rapid determination of hematocrit without the operator having to physically handle a blood-filled microhematocrit capillary tube. An even further advancement would be to have a rapid hematocrit that could easily become a commonly and safely gathered patient parameter so that medical personnel could be promptly and safely alerted to the medical needs of a trauma patient particularly in cases of internal bleeding or other emergencies. Advantageously, such a device could become a commonly carried physician tool so that the attending physician could automatically obtain his own hematocrit reading at the point of collection without handling the blood filled tube and without having to send the blood sample to the lab and then wait to obtain the hematocrit reading therefrom. Such a novel apparatus and method is disclosed and claimed herein.

BRIEF SUMMARY AND OBJECTS OF THE INVENTION

This invention includes a hand-held hematocrit reader having an ultrasound transducer and a photocell arrangement for automatically determining the hematocrit of a blood sample. An empty microhematocrit capillary tube is inserted into the reader and then filled with blood. The ultrasound transducer imposes a standing wave ultrasound field on the blood to cause the red blood cells to be forced into discrete, tightly packed bands separated by bands of plasma. This separation phenomena occurs within seconds and provides a rapid, accurate hematocrit of a blood sample. The hematocrit is read automatically and accurately using a photocell arrangement to determine the ratio of the red blood cells in the bands relative to the plasma between the bands. The device includes a calibration system for automatically calibrating the device each time it is used.

It is, therefore, a primary object of this invention to provide improvements in hematocrit reader apparatus.

Another object of this invention is to provide improvements in the method for obtaining an automatic hematocrit reading.

Another object of this invention is to provide an automatic hematocrit reader wherein a blood sample is remotely collected in a microhematocrit capillary tube and is then banded under the force of a standing acoustic wave with the hematocrit obtained thereby being automatically determined using a photocell system.

Another object of this invention is to provide an automatic hematocrit reader that is automatically calibrated each time it is used.

These and other objects and features of the present invention will become more readily apparent from the following description in which preferred and other embodiments of the invention have been set forth in conjunction with the accompanying drawing and appended claims.

DETAILED DESCRIPTION OF THE PREFERRED EMBODIMENT

Figure 1:
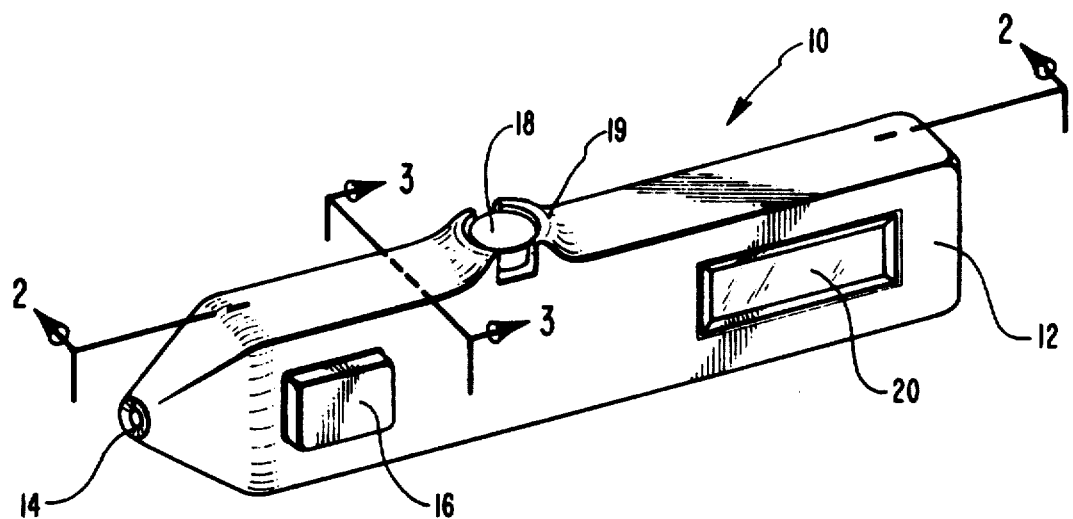
FIG. 1 is a perspective view of the automatic hematocrit reader apparatus of this invention.

The invention is best understood by reference to the drawing wherein like parts are designated by like numerals throughout in conjunction with the following description.

General Discussion

It has been known for at least fifteen years that red blood cells can be forced into "bands" when exposed to an ultrasonic standing wave field. This banding phenomena imparts a striated appearance to the blood. The banding or striation in the blood is caused by standing waves that force the blood cells into the pressure minima of the acoustic field so that bands or striations form at half wavelength intervals. For example, it has been found that an ultrasound transducer having an operating frequency in the range of one megahertz (1 MHz) will produce standing wave nodes and antinodes every 375 micrometers. This means that a blood sample having an hematocrit reading of 50% will result in a red blood cell band that is 375 micrometers wide and a plasma band that is also 375 micrometers wide. Correspondingly, an hematocrit of 25% will produce a red blood cell band about 190 micrometers wide and a plasma band that is about 560 micrometers wide.

The force exerted on a particle in an acoustic standing wave is given by the following formula:

$$F_a = \frac{V_o P_a^2 K \sin 2k z}{4\rho c^2} \left[ \frac{1}{\delta \sigma^2} - \left( \frac{5\delta - 2}{2\delta + 1} \right) \right]$$

where $V_o$ is the particle volume, $P_a$ is the pressure amplitude, $k_z = 2\pi/\lambda, \theta = c^*/c, \delta = \rho^*/\rho$, $c^*$ and $c$ are the sound velocities in the liquid droplet and medium while $\rho^*$ and $\rho$2 are the densities of the liquid droplet and suspending medium, respectively.

The ultrasonic standing wave force $F_a$, as evidenced by this equation, is a function of the particular volume, the pressure amplitude, the wave number, and the properties of the cells and the medium. This force is quite powerful and blood will form into "bands" within seconds after application of the acoustic field. The force $F_a$ "packs" the red blood cells very tightly together, just as a high speed centrifuge "packs" red blood cells into the bottom of a capillary tube. Accordingly, it is possible to use an ultrasonic standing wave to create a packed blood fraction which can then be measured as a function of the blood hematocrit reading.

Figure 5:
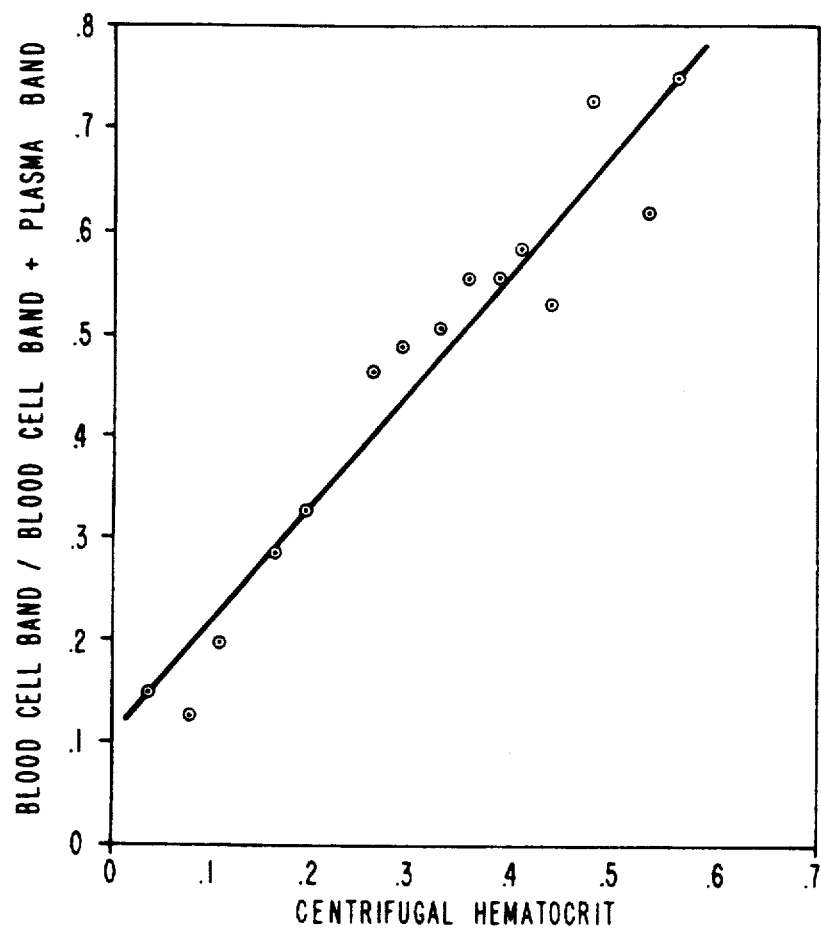
FIG. 5 is graph comparing hematocrit readings obtained using ultrasound with hematocrit readings obtained using conventional centrifugation.

An early prototype of this invention formed the bands and accurately measured the hematocrit reading provided thereby in 10 to 15 seconds. The accuracy of this invention as compared with a conventional centrifuge-based method is illustrated by the graph at FIG. 5, as will be discussed more fully hereinafter.

Blood will band readily in a microhematocrit tube if an ultrasound transducer is acoustically coupled to one end of the microhematocrit capillary tube. Experimentally we have constructed very compact acoustically coupled tube holders by cementing a cone-shaped, acoustic horn to a small (1/4") transducer. The efficiency of the acoustic coupling may be improved by changing the external profile of the acoustic horn to an exponential profile, for example. The end of the microhematocrit capillary tube is placed onto the acoustic horn so that the tube sealing compound makes contact with the acoustic horn.

Making the ultrasound transducer small increases its impedance and this lowers the power obtained for a given driving voltage. A larger transducer would provide better matching between the RF amplifier and the transducer, but this will lead to lost power around the tube and will lessen the holder compactness. A gel coupling agent can be used, as well as a liquid medium contained within seals.

A simple RF amplifier can be used to drive an ultrasonic transducer and optimized to drive a small (0.25 inch) high-impedance transducer used with a tube holder assembly. The amplifier design has been tested and at a frequency of 1.0 MHz the circuit caused distinct blood bands to form in 5–7 seconds in a microhematocrit capillary tube.

It is fairly straightforward to calculate hematocrit from banded blood such as produced using an ultrasound standing wave. The system computer need only count the number of "blood pixels," and divide this sum by the total number of data points, and multiply by 100. However, this straightforward description ignores some important issues. The data processed by the computer could be faulty. If the light source or the transducer driver failed, then no legitimate "image" is possible. The data memory of the computer might contain random bytes which could be used to calculate an erroneous hematocrit. In a less complete failure, a "shadow" effect could be produced in the data, due to a partial light or photocell failure.

Fortunately, the nature of the expected image lends itself to rigorous error checking. The number of blood/plasma bands is set by the frequency of the ultrasound and the length of the imaged tube. The spacing between the blood bands is also determined by the frequency of the ultrasound. If the number of blood and plasma bands is found to be correct, and the spacing of these bands is also found to be correct, then the data must represent a legitimate banded blood image.

The system software must determine whether a datum represents a "blood pixel" or a "plasma pixel". The software will then find all of the edges between the blood and plasma bands. The prototype software implemented the two functions just mentioned, checked the number of blood and plasma bands, and issued an error message if this number was not correct. The preliminary software did not verify that the spacing between the blood bands was correct, but the later software implemented this last error check as well.

It is possible that a few blood or plasma bands will not be imaged correctly due to lighting conditions, focusing, etc. The software will calculate the width of all blood and plasma bands. If a band is found whose width is more than three standard deviations from the mean width, then this blood/plasma band pair will be rejected and the amended data again tested. Only if a suitable number of blood/plasma bands are found whose widths all fall within three standard deviations of the mean will the hematocrit be calculated.

Another error check is a check on the "stability" of the data obtained. If the applied power is insufficient, we have observed that the blood bands will compress relatively slowly to their final width. This effect might also be produced if the blood sample is cold and more viscous. The present device will analyze the photocell data every second or so, and only process data which has been stable for some predetermined length of time. If the microcontroller observes that the bands take too long to stabilize, an error message can be printed that the battery charge is too low and is producing insufficient power. Of course, hardware checks of battery voltage and perhaps ultrasonic power levels will also be implemented.

Detailed Description

Figure 4:
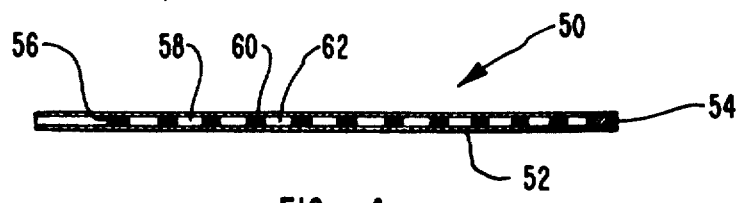
FIG. 4 is a cross sectional view of a conventional microhematocrit capillary tube.

Referring now more particularly to FIG. 1, the hematocrit reader apparatus of this invention is shown generally at 10 and includes a housing 12 with an inlet port 14 at the forward end with an adjacent interlock/eject button 16. A readout window 20 is located adjacent the other end of housing 12 and is configured as a conventional liquid crystal display 20 for displaying thereon the hematocrit. An upper edge of housing 12 includes an activation button 18 partially surrounded by a protective ridge 19. Hematocrit reader 10 is configured so that the operator (not shown) can hold hematocrit reader 10 in his or her hand and insert through inlet port 14 a microhematocrit capillary tube 50 (see FIG. 4) and obtain therefrom the hematocrit reading of a blood sample contained therein.

Figure 2:
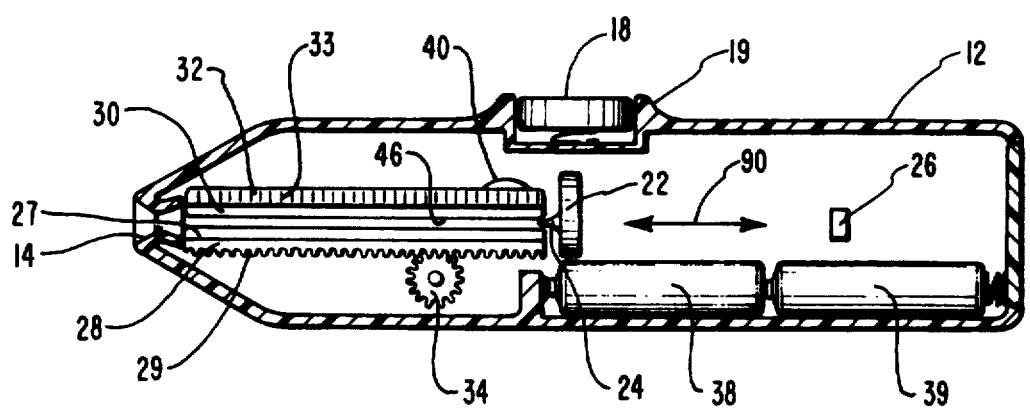
FIG. 2 is a greatly simplified schematic of a cross sectional view of the interior of the automatic hematocrit reader apparatus of FIG. 1 taken along lines 2—2.
Figure 3:
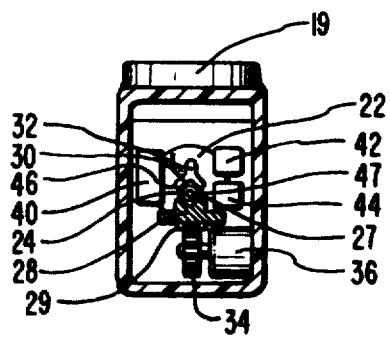
FIG. 3 is a schematic, cross sectional view taken along lines 3—3 of FIG. 1.

Referring now more particularly to FIGS. 2 and 3, a microhematocrit capillary tube-receiving chamber 27 is shown as a trough 28 having a V-shaped cross section (best seen in FIG. 3) into which the microhematocrit capillary tube 50 (FIG. 4) is guidingly received. Superimposed above trough 28 is a corresponding guide 30 having an inverted, generally Y-shaped cross section (best seen in FIG. 3). The space between trough 28 and guide 30 creates chamber 27. It will be noted that the sides of chamber 27 as defined by V-shaped trough 28 and the sides of the inverted, Y-shaped guide 30 are open to provide longitudinal slots 46 and 47 on each side of the tube-receiving chamber 27 created thereby. The stem of the Y-shaped guide 30 is configured from a clear plastic material and forms a calibration step 32 having a plurality of evenly spaced indicia 33 thereon for calibration purposes as will be discussed more fully hereinafter.

A light source 40 is mounted on one side of chamber 27 adjacent the rear thereof while directly opposed from light source 40 are photodetectors 42 and 44. Photodetector 42 is placed in juxtaposition with calibration member 32 while photodetector 44 is placed in juxtaposition adjacent slot 47.

An ultrasound transducer 22 having an acoustic horn 24 mounted thereon is positioned on the end of trough 28 with acoustic horn 24 in alignment with the end of chamber 27. Acoustic horn 24 is adapted to engage the end of microhematocrit capillary tube 50 (FIG. 4) so as to acoustically couple ultrasonic energy emitted by ultrasound transducer 22 with blood 58 (FIG. 4) in microhematocrit capillary tube 50.

Operationally, microhematocrit capillary tube 50 is inserted through inlet port 14 where it is received in chamber 27 until it is placed into abutment against acoustic horn 24. A sensor built into acoustic horn 24 provides an audible signal to indicate acoustic coupling between ultrasound transducer 22 and microhematocrit capillary tube 50.

Figure 6:
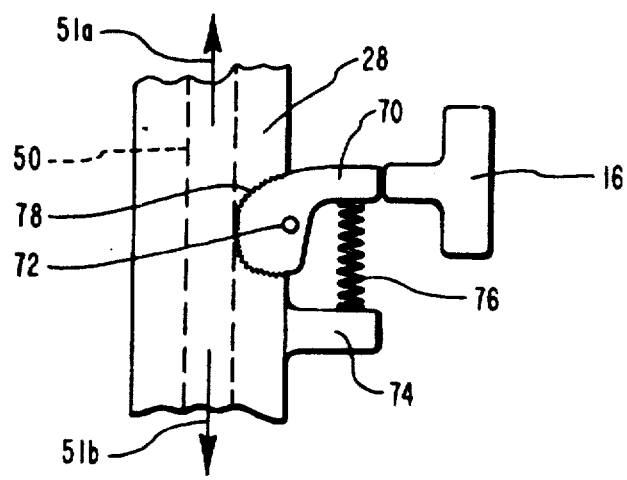
FIG. 6 is an enlarged, fragmentary view of the interlock/ejection system for the microhematocrit capillary tube.

Referring now more particularly to FIG. 6, to insert microhematocrit capillary tube 50, button 16 is depressed which in turn pivots cam 70 around pivot 72 to bring cam surface 78 away from the path of travel of microhematocrit capillary tube 50. When the end of microhematocrit capillary tube 50 strikes acoustic horn 24 a signal is received and button 16 is released allowing spring 76 to pull the arm of cam 70 toward post 74 bringing cam surface 78 tightly against microhematocrit capillary tube 50. Cam surface 78 is configured with a resilient surface so as to provide a nonslip surface to cam surface 78. Spring 76 pulls against cam 70 so that cam surface 78 forces microhematocrit capillary tube 50 toward acoustic horn 24 (FIG. 2) as indicated by arrow 51a. In this manner microhematocrit capillary tube 50 is spring biased into engagement with acoustic horn 24 to assure good acoustic coupling therewith. Release of microhematocrit capillary tube 50 is accomplished by depressing button 16 which in turn forces cam 70 to rotate around pivot 72 causing cam surface 78 to push against microhematocrit capillary tube 50 and move it slightly in the direction of arrow 51b.

Referring again to FIGS. 2 and 3, trough 28 includes a rack gear 29 that cooperates with a pinion gear 34 mounted on electric motor 36. The entire assembly of trough 28, guide 30 and ultra sound transducer 22 are moved back and forth by the cooperation of rack and pinion gears 29 and 34 as indicated by arrow 90. Electric motor 36 (FIG. 3) turns pinion gear 34 to move this entire assembly as indicated. Rearward travel of this assembly is stopped by a limit switch 26 which, in turn, creates reversal within electric motor 36 to return the entire assembly of chamber 27 to its original position. Electrical energy is supplied by batteries 38 and 39.

In operation, microhematocrit capillary tube 50 (FIG. 4) is inserted through inlet port 14 and is received within chamber 27 until the end thereof, plug 54, engages acoustic horn 24. At that time a signal is transmitted indicating that the microhematocrit capillary tube 50 is properly in place. Release of button 16 causes cam surface 78 to engage microhematocrit capillary tube 50, as described hereinbefore, urging it under a spring bias against acoustic horn 24.

Figure 7:
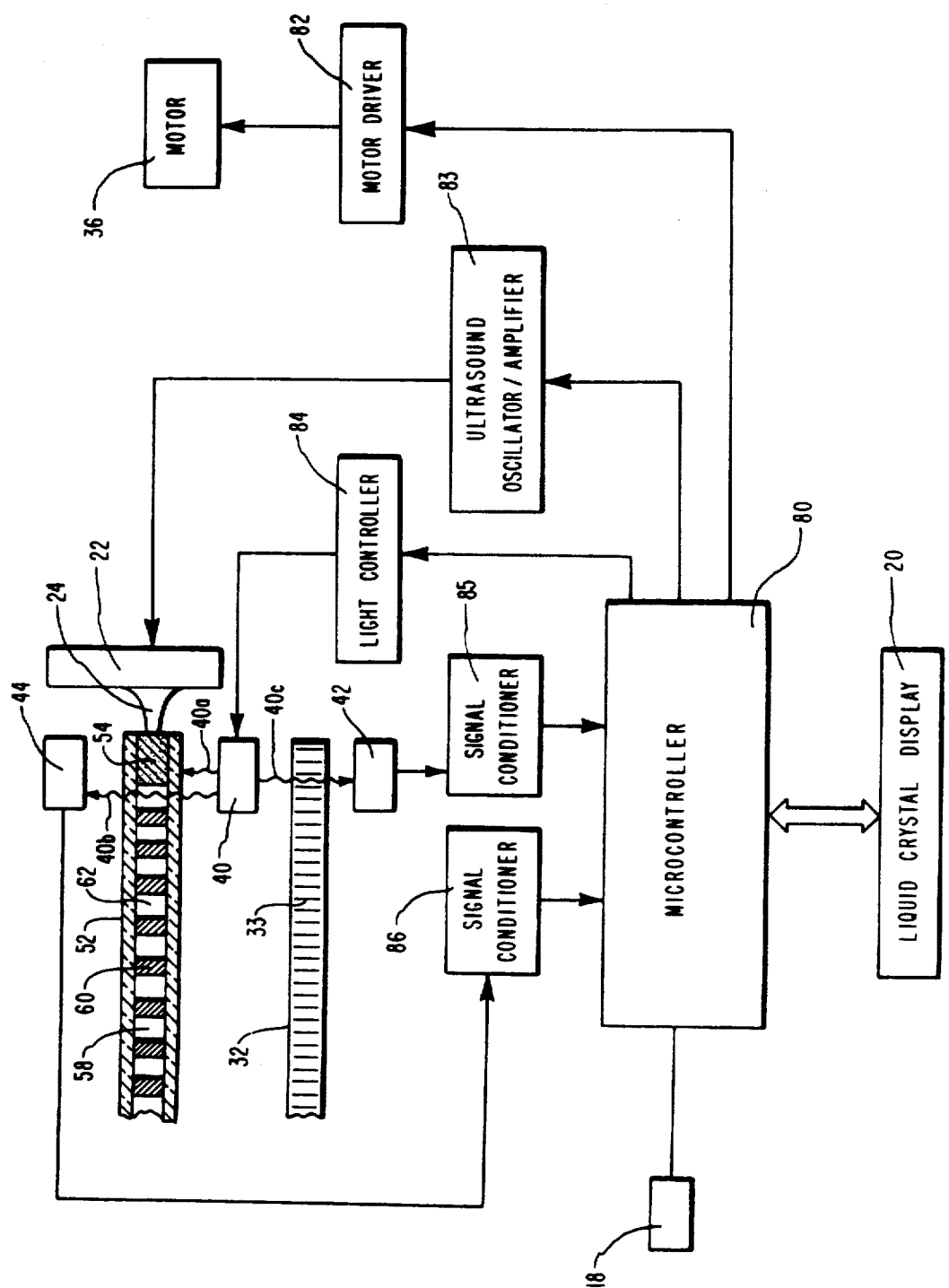
FIG. 7 is a schematic circuit for the hematocrit reader of this invention.

The operator (not shown) then touches the end of microhematocrit capillary tube 50 to a drop of blood (not shown) resulting in blood 58 being drawn into microhematocrit capillary tube 50 as shown. A light ray 40b (FIG. 7) emitted by light source 40 is received by photodetector 44 until blood sample 58 reaches plug 54 at which time the blood 58 interferes with light ray 40b. A second signal is thus generated indicating that microhematocrit capillary tube 50 is filled with blood 58. At that time microcontroller 80 transmits a signal to ultrasound oscillator/amplifier 83 which, in turn, drives ultrasound transducer 22 with the ultrasound energy emitted thereby being acoustically coupled into blood 58 by acoustic horn 24. As described hereinbefore, the ultrasonic energy coupled into blood 58 is reflected by meniscus 56 (FIG. 4) and results in a standing wave being formed inside microhematocrit capillary tube 50. The resulting bands of packed red blood cells 60 and bands of plasma 62 give microhematocrit capillary tube 50 a banded appearance.

After a suitable time delay, microcontroller 80, activates motor driver 82 which in turn energizes electric motor 36 causing pinion gear 34 to rotate moving rack gear 29 at a constant rate of motion until limit switch 26 is reached at which time motor driver 82 is reversed causing motor 36 to reverse pinion gear 34 thereby returning rack gear 29 to its original position. During this translational movement as indicated by arrow 90 light source 40 emits light rays 40a and 40b through microhematocrit capillary tube 50 with the alternating bands of packed red blood cells 60 and plasma 62 resulting in changes in the signal received by signal conditioner 86. The resulting hematocrit is then displayed on liquid crystal display 20.

Calibration of the apparatus is automatically provided through calibration strip 32 having calibration indicia 33 marked thereon. In particular, light rays 40c from light source 40 pass through calibration strip 32 where they are periodically interrupted by calibration indicia 33 with a resulting signal being detected by photodetector 42 and processed by signal conditioner 85. The signal comparison between the signal received by signal conditioner 86 and the signal received by signal conditioner 85 is electronically compared by microcontroller 80 so as to provide an accurate indication of the hematocrit of blood sample 58 within microhematocrit capillary tube 50.

The Method

In practicing the method of this invention, the operator (not shown) grasps microhematocrit reader 10 and depresses button 16 actuating cam surface 78 away from engagement with microhematocrit capillary tube 50. An empty microhematocrit capillary tube 50 is inserted into chamber 27 until the end thereof strikes acoustic horn 24. The foregoing first signal is received at which time button 16 is released allowing spring 76 to rotate cam 78 against microhematocrit capillary tube 50 urging the same in the direction indicated by arrow 51a. With microhematocrit capillary tube 50 resiliently urged against acoustic horn 24 the operator is ready to obtain and read the hematocrit of a blood sample.

Button 18 is depressed to illuminate light source 40 and then the end of microhematocrit capillary tube 50 is brought into contact with a sample of blood 58 and the same is drawn into microhematocrit capillary tube 50 by capillary action as is customary. The incoming blood 58 blocks light ray 40b emitted by light source 40 resulting in a second signal being produced by photodetector 44 and signal conditioner 86. When the blood 58 has blocked light ray 40b resulting in the second signal, microcontroller 80 activates ultrasound oscillator/amplifier 83 so that ultrasonic energy is emitted by ultrasound transducer 22. The ultrasound energy emitted thereby is transmitted through acoustic horn 24 into blood 58 resulting in banding of blood 58 into bands of red blood cells 60 and bands of plasma 62. After a preselected interval of time (five to ten seconds) microcontroller 80 then sends a signal to motor driver 82 which causes electric motor 36 to rotate so that pinion gear 34 in engagement with rack gear 29 moves the entire assembly to the right in FIG. 2 until it comes engagement with limit switch 26 at which time motor driver 82 automatically reverses motor 36 resulting in a return motion of the entire assembly to its original position depicted in FIG. 2.

During the foregoing translational movement illustrated by arrows 90 microhematocrit capillary tube 50 and calibration strip 32 are moved between light source 40 and photodetectors 42 and 44, respectively. The relative of the alternating bands of packed red blood cells 60 and bands of plasma ,62 result in periodic changes in the light received by photodetector 44. The rate of travel and the duration of the blockage and transmittal of light beams 40a and 40b is interpreted by signal conditioner 86 as a function of the hematocrit within blood 58. Calibration of the system is provided by calibration strip 32 and evenly spaced calibration indicia 33 thereon which interrupt light ray 40c on a regular basis as detected by photodetector 42 and processed by signal conditioner 85. In this way changes in the speed of motor 36 can be readily detected and compensated for by the means of calibration strip 32. The signal comparison between the signals produced by signal conditioner 86 with those produced by signal conditioner 85 are then compared within microcontroller 80 so as to provide an accurate determination of the hematocrit within microhematocrit capillary tube 50. The resulting hematocrit is then displayed on liquid crystal display 20.

At the completion of the foregoing cycle, microhematocrit capillary tube 50 is back at its original position protruding from inlet port 14. Button 18 is then released and button 16 again depressed which causes cam surface 78 to rotate counterclockwise against microhematocrit capillary tube 50 causing the same to be released and to be partially ejected out of inlet 14. Thereafter, the operator (not shown) merely upends hematocrit reader 10 over a waste receptacle allowing gravity to pull microhematocrit capillary tube 50 out of microhematocrit reader 10.

In this manner, the operator (not shown) is not required to touch microhematocrit capillary tube 50 in any manner thus completely eliminating any danger of accidental contact between blood 58 and the operator. Accordingly, the danger of accidental breakage of microhematocrit capillary tube 52 (FIG. 4) with its resultant attendant risk of puncture is completely eliminated to the safety of the operator. Advantageously, this safety feature is also coupled with a very rapid, safe, and accurate reading of the hematocrit of the blood sample processed thereby.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed and desired to be secured by United States Letters Patent is:

1. An automatic hematocrit reader comprising:

receiving means for receiving a microhematocrit capillary tube, said microhematocrit capillary tube capable of receiving a sample of blood;

an ultrasonic transducer;

banding means for banding said sample of blood into bands of red blood cells and bands of plasma comprising coupling means for acoustically coupling said sample of blood to said ultrasonic transducer and generating a standing wave in said sample of blood with ultrasonic energy produced by said ultrasonic transducer;

detection means for detecting a first relative width of said bands of red blood cells to a second relative width of said bands of plasma, said detection means also comprising a light source and a first photodetector for detecting when said sample of blood has reached a predetermined point in said microhematocrit capillary tube and a calibration means comprising a calibration strip and a second photodetector with said calibration strip interposed between said light source and said second photodetector;

comparison means for electronically comparing said first width with said second width to provide a calculation of the hematocrit of said sample of blood; and display means for displaying said hematocrit.

2. The automatic hematocrit reader defined in claim 1 wherein said receiving means comprises an engagement means for engaging said microhematocrit capillary tube in acoustic coupling with said ultrasonic transducer.

3. The automatic hematocrit reader defined in claim 1 wherein said engagement means comprises a cam springbiased in contact with said microhematocrit capillary tube.

4. The automatic hematocrit reader defined in claim 1 wherein said light source, said first photodetector, and said second photodetector are stationary with said microhematocrit capillary tube and said calibration strip being longitudinally movable between said light source and said first and second photodetectors at a preselected rate of travel thereby determining said hematocrit with said first photodetector and calibrating said first photodetector with said calibration strip and said second photodetector.

5. The automatic hematocrit reader defined in claim 1 wherein said display means comprises a liquid crystal display for displaying said hematocrit.

6. An automatic hematocrit reader for obtaining the hematocrit of a sample of blood in a microhematocrit capillary tube without the operator having to touch the microhematocrit capillary tube comprising:

a chamber for releasably receiving a microhematocrit capillary tube, the chamber comprising a carriage for moving said microhematocrit capillary tube longitudinally an incremental distance; - a light source mounted on one side of said chamber and configured to shine a light through said chamber as said carriage is moved through said incremental distance, said light source including a second photodetector mounted on the other side of said carriage, said carriage including a calibration strip interposed between said light source and said second photodetector, a first photodetector mounted on the other side of said chamber in alignment with light from said light source;

an ultrasonic transducer mounted at the end of said chamber so as to be acoustically coupled to said microhematocrit capillary tube inserted in said chamber;

motor means for moving said carriage through said incremental distance; and electronic signal processing means for processing electronic signals generated by said first photodetector.

7. The automatic hematocrit reader defined in claim 6 wherein said chamber includes mechanical means for mechanically engaging said microhematocrit capillary tube to hold said microhematocrit into acoustic coupling with said ultrasonic transducer.

8. The automatic hematocrit reader defined in claim 6 wherein said ultrasonic transducer includes sensing means for sensing when a microhematocrit capillary tube is acoustically coupled to said ultrasonic transducer, sensing means including a signal means for signaling when said microhematocrit capillary tube is acoustically coupled to said ultrasonic transducer.

9. The automatic hematocrit reader defined in claim 6 wherein said first photodetector includes sensing means for sensing when a sample of blood has reached the end of said microhematocrit capillary tube, said sensing means including signal means for signaling when said sample of blood has reached the end of said microhematocrit capillary tube.

10. The automatic hematocrit reader defined in claim 6 wherein said engagement means includes ejection means for ejecting said microhematocrit capillary tube.

11. A method for obtaining the hematocrit of a sample of blood comprising:

preparing a chamber for a microhematocrit capillary tube, said chamber including a carriage for said microhematocrit capillary tube, said carriage having a slot for transmitting light through said carriage, said chamber having an ultrasonic transducer at the end of said chamber to be acoustically coupled to said microhematocrit capillary tube when said microhematocrit capillary tube is inserted into said chamber;

mounting a light source on one side of said chamber for transmitting light from said light source through said carriage;

orienting a first photodetector on the other side of said chamber so as to receive said light transmitted through said carriage;

electronically coupling said first photodetector to an electronic computation means for computing the light signals receive by said first photodetector;

affixing a calibration strip on said carriage in juxtaposition with said light source and placing a second photodetector across from said light source so that light from said light source passes through said calibration strip;

inserting an empty microhematocrit capillary tube into said chamber into acoustic coupling at a first end with said ultrasonic transducer, a second end of said microhematocrit capillary tube extending beyond said chamber;

drawing a sample of blood into said microhematocrit capillary tube through said second end;

banding said sample of blood by creating a standing wave in said sample of blood with said ultrasonic transducer;

moving said microhematocrit capillary tube longitudinally past said light source while also moving said calibration strip between said light source and said second photodetector thereby providing a calibration signal for said electronic computing means, said banding creating signal changes in said first photodetector;

calculating hematocrit electronically with said electronic computation means from said signal changes; and displaying said hematocrit.

* * * * *